United States Patent
Perez et al.

(10) Patent No.: US 11,211,157 B2
(45) Date of Patent: Dec. 28, 2021

(54) USING EMOTIONAL MAPS AND DIALOG DISPLAY TECHNOLOGY TO IMPROVE WORKOUT EXPERIENCES

(71) Applicant: Intel Corporation, Santa Clara, CA (US)

(72) Inventors: Guillermo Perez, Seville (ES); Israel Perez Tudela, Alcalá del Río (ES)

(73) Assignee: Intel Corporation, Santa Clara, CA (US)

( * ) Notice: Subject to any disclaimer, the term of this patent is extended or adjusted under 35 U.S.C. 154(b) by 488 days.

(21) Appl. No.: 15/396,243

(22) Filed: Dec. 30, 2016

(65) Prior Publication Data

US 2018/0185705 A1 Jul. 5, 2018

(51) Int. Cl.
*G16H 20/30* (2018.01)
*G09B 19/00* (2006.01)
*G16H 40/63* (2018.01)
*G16H 50/30* (2018.01)
*G16H 20/70* (2018.01)

(52) U.S. Cl.
CPC ......... *G16H 20/30* (2018.01); *G09B 19/0038* (2013.01); *G16H 20/70* (2018.01); *G16H 40/63* (2018.01); *G16H 50/30* (2018.01)

(58) Field of Classification Search
CPC ........... A63B 24/0075; A63B 71/0619; G16H 20/30; G16H 40/63; G16H 50/30; G16H 20/70; G09B 19/00
See application file for complete search history.

(56) References Cited

U.S. PATENT DOCUMENTS

| | | | |
|---|---|---|---|
| 8,398,546 B2* | 3/2013 | Pacione | A61B 5/411 128/920 |
| 8,719,202 B1* | 5/2014 | Maeng | G06F 19/3481 706/45 |
| 9,384,661 B1* | 7/2016 | DeLuca | G08G 1/096838 |
| 2006/0183980 A1* | 8/2006 | Yang | A61B 5/0022 600/301 |
| 2009/0106049 A1* | 4/2009 | Breslau | G06Q 50/22 705/3 |
| 2009/0210280 A1* | 8/2009 | Jin | G06F 19/3481 705/7.13 |
| 2013/0006521 A1* | 1/2013 | Needham | G01C 21/3476 701/426 |

(Continued)

OTHER PUBLICATIONS

The Free Dictionary, https://www.thefreedictionary.com/emotion (last visited May 14, 2021).*

*Primary Examiner* — Malina D. Blaise
(74) *Attorney, Agent, or Firm* — Jordan IP Law, LLC

(57) ABSTRACT

Systems, apparatuses and methods may provide for technology to improve a workout experience of a user by determining an emotional state of the user, identifying a workout route based on the emotional state of the user, and outputting the workout route via a user interface device. Additionally, determining the emotional state of the user may include inferring emotions from one or more sensor information or user speech information. In one example, the sensor information includes one or more of blood pressure signals, heart rate signals or sweat measurement signals and the user speech information includes one or more of words used in an input utterance or a prosody of the input utterance.

26 Claims, 9 Drawing Sheets

(56) References Cited

U.S. PATENT DOCUMENTS

| | | | |
|---|---|---|---|
| 2014/0309849 A1* | 10/2014 | Ricci | B60Q 1/00 701/33.4 |
| 2014/0316805 A1* | 10/2014 | Nagata | G06F 19/36 705/2 |
| 2015/0037771 A1* | 2/2015 | Kaleal, III | G09B 5/02 434/257 |
| 2015/0081210 A1* | 3/2015 | Yeh | A61B 5/7415 701/428 |
| 2015/0199494 A1* | 7/2015 | Koduri | G06F 19/00 700/91 |
| 2015/0238815 A1* | 8/2015 | Lee | G01C 21/343 701/533 |
| 2015/0251074 A1* | 9/2015 | Ahmed | A61B 5/02405 700/91 |
| 2015/0351655 A1* | 12/2015 | Coleman | A61B 5/0482 600/301 |
| 2016/0058367 A1* | 3/2016 | Raghuram | A61B 5/486 600/479 |
| 2016/0086500 A1* | 3/2016 | Kaleal, III | G06T 19/00 434/257 |
| 2016/0196758 A1* | 7/2016 | Causevic | G09B 5/00 434/236 |
| 2016/0232131 A1* | 8/2016 | Liu | G06F 17/211 |
| 2016/0234595 A1* | 8/2016 | Goran | H04R 3/002 |
| 2016/0375306 A1* | 12/2016 | Gu | A63B 24/0021 701/430 |
| 2017/0030726 A1* | 2/2017 | French | G01C 21/3461 |
| 2017/0095674 A1* | 4/2017 | Hresko | A61N 1/3993 |
| 2017/0153636 A1* | 6/2017 | Boesen | G06F 1/163 |
| 2017/0213470 A1* | 7/2017 | Briggs | G09B 5/125 |
| 2018/0027371 A1* | 1/2018 | Austraat | H04L 67/22 455/456.3 |
| 2018/0170392 A1* | 6/2018 | Yang | B60W 40/09 |
| 2018/0182105 A1* | 6/2018 | Liao | G06T 11/00 |
| 2018/0184893 A1* | 7/2018 | Sahler | A61B 3/032 |
| 2019/0197073 A1* | 6/2019 | Liu | G06F 16/9535 |

\* cited by examiner

400

| Route Segment | Tags | Emotions | Previously Followed | Route Source | Weight |
|---|---|---|---|---|---|
| Path A | Landscape | Stress | No | User 2 | 0.8 |
| Path B | Traffic | Happy | Yes | User 1 | 0.0 |
| Path C | Noise | Bored | No | User 1 | 1.0 |

|  | | SOURCE | |
|---|---|---|---|
|  | | User 1 | Not User 1 |
| HISTORY | Previously Followed | 0 | 0 |
|  | Not Previously Followed | 1 | 0.8 |

Weight = F (Source +previously followed)

USING EMOTIONAL MAPS AND DIALOG DISPLAY TECHNOLOGY TO IMPROVE WORKOUT EXPERIENCES

TECHNICAL FIELD

Embodiments generally relate to workout technology. More particularly, embodiments relate to using emotional maps and dialog systems to improve workout experiences.

BACKGROUND

Workouts for runners and cyclists may rely heavily on the physical distribution of the area where the athlete is training. For any given workout session, the athlete may perform it along a route that has a certain distance, provides a target level of difficulty and is feasible in terms of traffic, etc.

Automated coaching dialogue systems (e.g., software running in a smartphone with a dialogue system trained as a coach) may define workout plans but rely on the athlete/sportsman to choose the best route to apply. The dialogue systems may also give directions on the general characteristics of the workout for that day and let the athlete find the route that is suitable for his or her workout. While these systems may be suitable under certain circumstances, there remains considerable room for improvement.

BRIEF DESCRIPTION OF THE DRAWINGS

The various advantages of the embodiments will become apparent to one skilled in the art by reading the following specification and appended claims, and by referencing the following drawings, in which:

FIG. 4 is an illustration of an example of an emotional maps database shared by a community of users according to an embodiment.

FIG. 5 an illustration of an example of a weighting policy shared by a community of users according to an embodiment.

DESCRIPTION OF EMBODIMENTS

Figure 1:
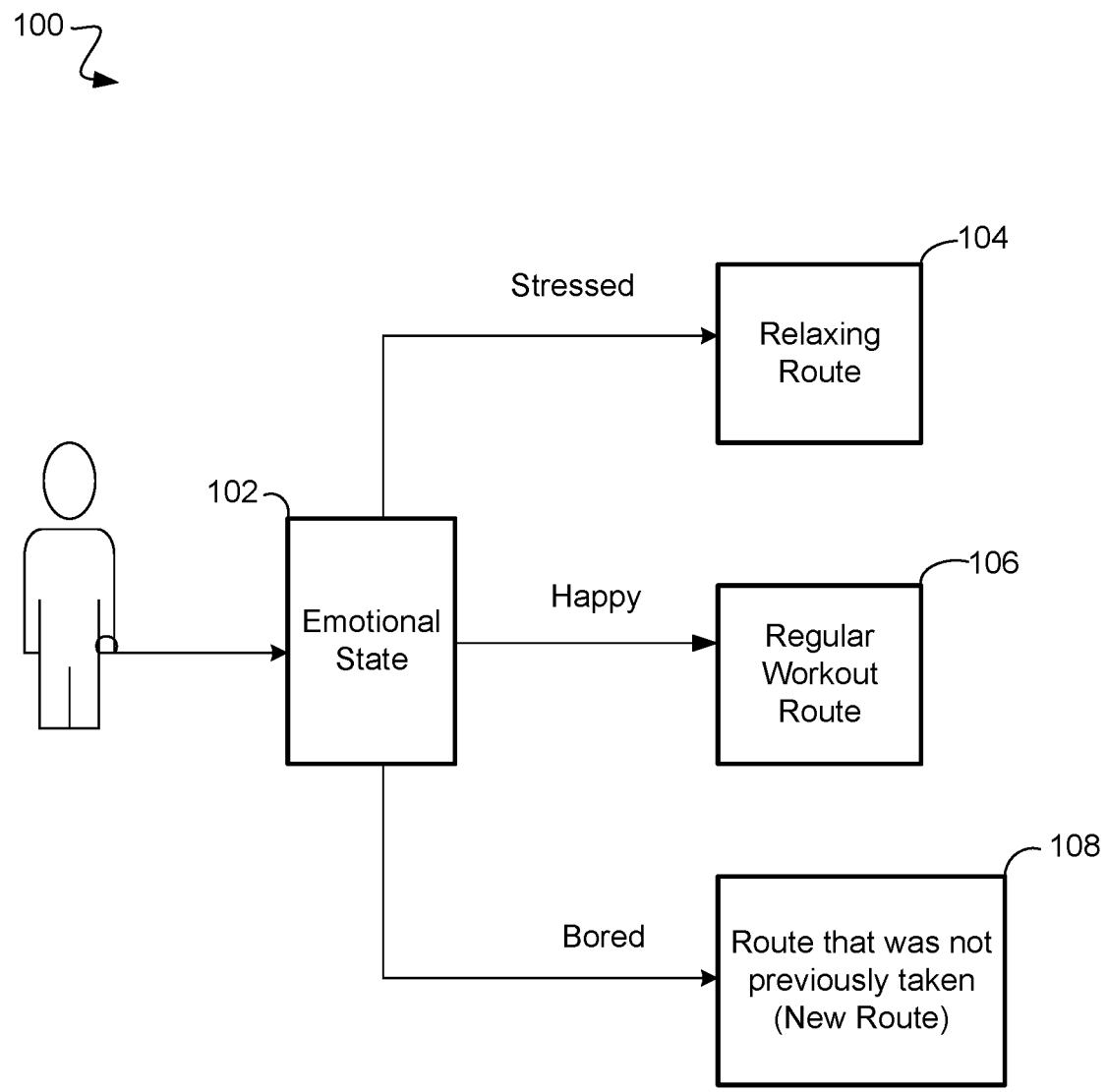
FIG. 1 is an illustration of an example of workout route generation scenario based on user emotional states according to an embodiment.

FIG. 1 illustrates an example of a workout route generation scenario 100 in which a workout route is generated based on user emotional states. For example, when it is detected that an emotional state 102 of a user is "Stressed", a relaxing route 104 may be generated by an automated coaching system (not shown) as a potential/recommended workout route. The relaxing route 104 might include, for example, a quiet and pleasant route, or as route with a natural landscape, and so forth. In another example, when it is detected that the emotional state 102 of the user is "Happy", a regular workout route 106 may be generated by the automated coaching system as a potential workout route. The regular workout route 106 might include, for example, paths, streets, roads, turns, etc., that the user typically follows when exercising. In yet another example, when the automated coaching system detects that the emotional state 102 of the user is "Bored", a new route 108 (e.g., that was not previously taken) may be generated as a potential work out route. Accordingly, the illustrated solution empowers the automated coaching system with the emotional state of the user, so that the workout route is adapted to the user preferences and moods.

Figure 2:
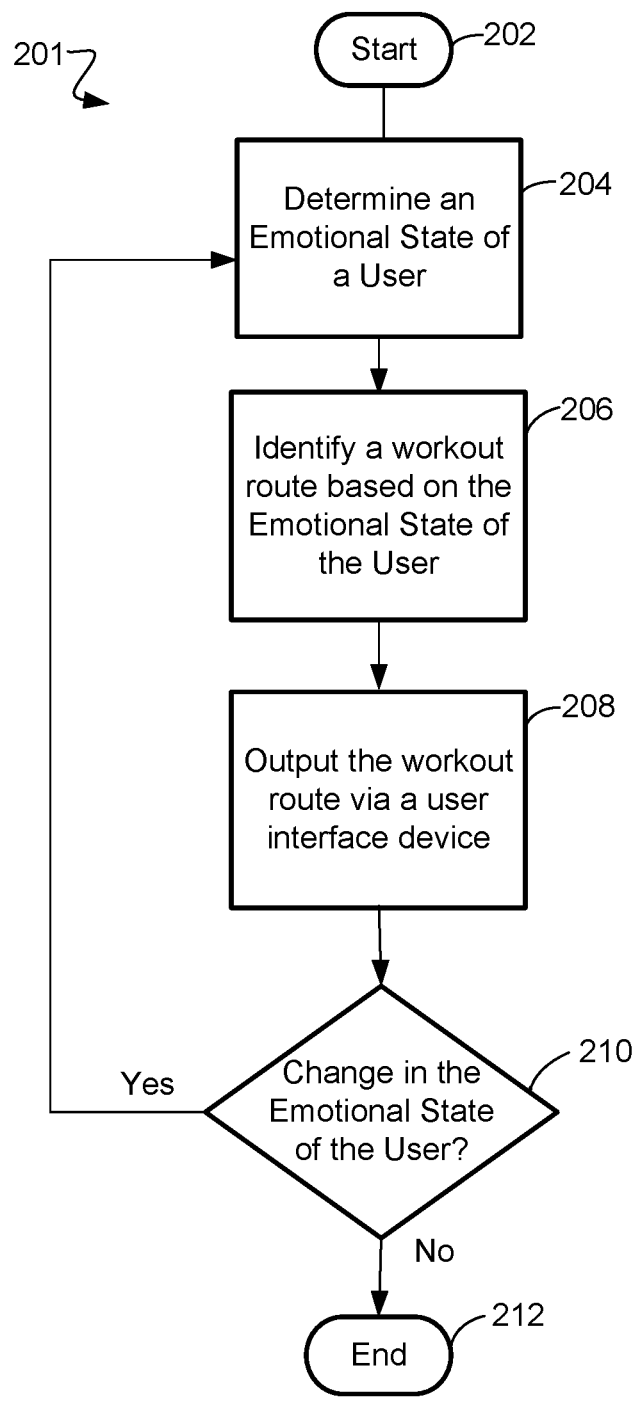
FIG. 2 is a flowchart of an example of a method of operating an automated coaching system according to an embodiment.

FIG. 2 illustrates a flowchart of an example of a method 201 of operating an automated coaching system according to an embodiment. The method 201 may be implemented as one or more modules in a set of logic instructions stored in a non-transitory machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof.

For example, computer program code to carry out operations shown in method 201 may be written in any combination of one or more programming languages, including an object-oriented programming language such as C#, JAVA or the like. Additionally, logic instructions might include assembler instructions, instruction set architecture (ISA) instructions, machine instructions, machine dependent instructions, microcode, state-setting data, configuration data for integrated circuitry, state information that personalizes electronic circuitry and/or other structural components that are native to hardware (e.g., host processor, central processing unit/CPU, microcontroller, etc.).

Illustrated processing block 202 starts operation of the automated coaching system. In illustrated processing block 204, the system determines an emotional state of a user (e.g., stressed, happy, sad, bored, etc.). Determining the emotional state of the user may include, for example, inferring emotions from one or more of sensor information or user speech information. The sensor information may include, for example, blood pressure signals, heart rate signals, sweat measurement signals, etc., or any combination thereof. The user speech information might include, for example, words used in an input utterance, a prosody of the input utterance, etc., or any combination thereof.

Based on the emotional state of the user, block 206 may identify a workout route. In illustrated processing block 208, the apparatus may output the workout route via a user interface (UI) device, wherein the user interface device may include a display, speaker(s), vibration subsystem (e.g., haptic motor), printer, or other wearable/fitness UI device.

In illustrated processing block 210, if the coaching system determines that there is change in the emotional state of the user, the system automatically updates the emotional state of the user in illustrated processing block 204. If there is no change in the emotional state of the user, the coaching system may terminate the method 201 in illustrated processing block 212.

Another example of dynamic update may arise from the user deviating from the predefined route. In such a case, the system may ask why the user decided to do so, and update emotional map information accordingly. For instance, the user may answer that she found the route very noisy and the system could add this piece of information to an emotional map database, as will be discussed in greater detail.

Figure 3:
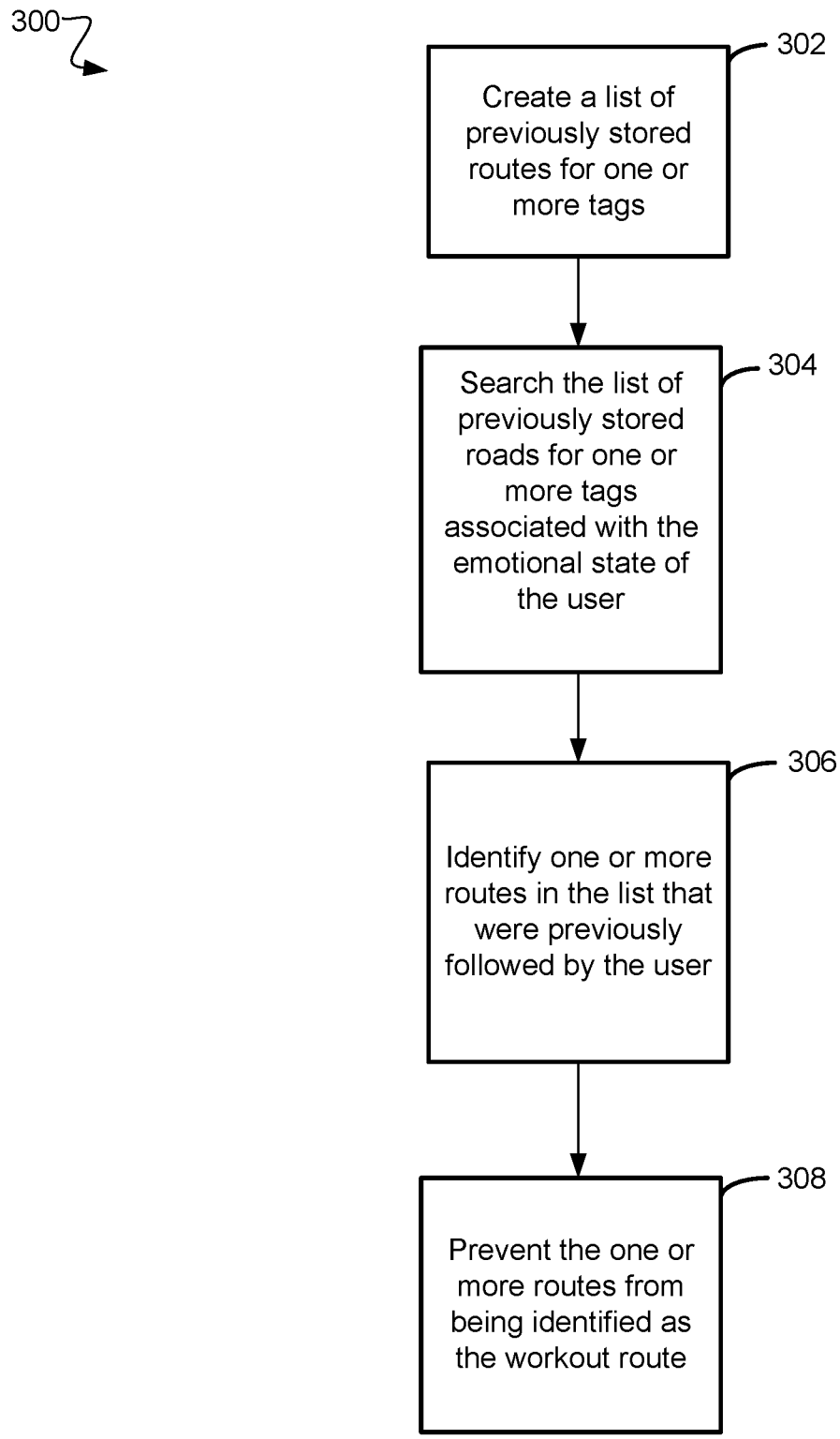
FIG. 3 is a flowchart of an example a method of creating a workout route based on user preference and mood according to an embodiment.

FIG. 3 is a flowchart of an example of a method 300 of creating workout routes based on user preferences and moods according to an embodiment. The method 300 may be implemented as one or more modules in a set of logic instructions stored in a non-transitory machine- or computer-readable storage medium such as RAM, ROM, PROM, firmware, flash memory, etc., in configurable logic such as, for example, PLAs, FPGAs, CPLDs, in fixed-functionality hardware logic using circuit technology such as, for example, ASIC, CMOS or TTL technology, or any combination thereof.

In illustrated processing block 302, the coaching system creates a list of previously stored routes for one or more tags. The tags may be generated by the coaching system from previously used keywords. Examples tags might include, for example, landscape, traffic, noise, etc., or any combination thereof. In illustrated processing block 304, the coaching system searches the list of previously stored roads for one or more tags associated with the emotional state of the user. When searching the list of previously stored routes, the system may prompt the user for specific routes in which the user is interested. For example, block 304 may determine that the user is interested in a quiet and pleasant route, a route with natural landscapes, a tourist route, etc.

In illustrated processing block 306, the automated coaching system, in response to searching the list of previously stored roads by the user, identifies one or more routes in the list that were previously followed. Block 306 may use historical information stored in local memory or retrieved from a remote source (e.g., server, cloud computing infrastructure). In illustrated processing block 308, the automated coach apparatus prevents the one or more previously followed routes form being identified as the workout route. Thus, by ensuring that the user does not repeat the same path to a point of boredom, block 308 may increase the likelihood that long-term fitness goals are achieved.

An example of the impact of the illustrated processing block 308 is the following: the user might ask to perform a cycling workout through a touristic route, wherein the community may rank a given path as the most interesting one from a touristic point of view. The illustrated solution may suggest, however, a different route because the highly-ranked route was followed by the user in a previous workout.

FIG. 4 an illustration of an example of an emotional maps database 400 that may be shared by a community of users (e.g., amateur and/or professional athletes) according to an embodiment. Emotional maps may generally be preconfigured routes shared by the community of athletes and tagged according to a number of factors such as, for example, landscape, traffic, noise, etc., as illustrated in the second "Tags" column of the database 400. An automated coaching dialog system may give a higher weight to the feedback provided by the athlete using the system. For example, in the last "Path C" row of the table 400, the tag is "Noise" with "Bored" as a detected emotion (e.g., emotional state). In the illustrated example, because the path was not previously followed by the athlete using the system ("User 1"), the system may assign a highest weight (e.g., "1.0") to the route as feedback to User 1. As another example, in the middle "Path B" row of the table 400, the tag is "Traffic" with "Happy" as a detected emotional state. Because the path was previously followed by User 1, the system may assign a lowest weight (e.g., "0.0") as a feedback to User 1. As another example, in the first "Path A" row of the table 400, the tag is "Landscape" with "Stress" as a detected emotional state. Because the path was obtained from another athlete (User 2) and the path was not previously followed by User 1, the system may assign an intermediate weight (e.g., "0.8") as a feedback to the User 1.

The emotional information may therefore work in two ways:

From the route's point of view in which potential routes are pre-classified as "emotional maps" following the feedback provided by other users. The system may have a set of alternatives ranked according to several "emotional" criteria (pleasantness, beauty, etc.). Since the criteria are subjective, the ranking may be based on the average of the user feedback.

From the user's point of view in which the system is able to determine what sort of route the user is interested in at any given time. For instance, after a stressful day of work, the user may say "I want to do my workout in a quiet route, please" or the system may automatically detect that the user is stressed based on sensor data.

The system may use the accumulated information when planning the workout and adapt to the preferences of the user. The route may also be updated in real-time during the workout. The update may be conducted as a result of a direct request from the user (e.g., "I would like to change to a more beautiful route"), an indirect observation ("This route is really ugly"), an inferred emotional from sensor data, etc., or any combination thereof.

As already noted, the route may also be updated without even an indirect input from the user. For example, the system may decide to do so based on the output of a sentiment analysis module (e.g., sentiment analyzer). For instance, the sentiment analysis module may point to a high level of stress in the athlete, making the system decide to select a more relaxing route. Alternatively, the sentiment analysis module may point to a sad mood, making the system suggest a livelier path.

The sentiment analysis module may automatically develop conclusions from inputs such as the words chosen by the user or the prosody of captured speech. Also, in the specific fitness context at hand, other sources of information may be used such as, for example, the type of music selected for the workout (if any), sensor information (heart-rate, sweat, etc.), and so forth.

Another example of a dynamic update may arise from the user deviating from the predefined route. As already noted, the system may ask the user why he or she decided to do so, and update the emotional map information accordingly. For instance, the user may answer that she found the route very noisy and the system could add this piece of information to the emotional map database.

Another emotional factor that the system may take into account is boredom. It may be important for the long-term success of a training plan that the user sticks to the plan until its end, so avoiding boredom may be particularly advantageous. The technology described herein may prevent this risk by taking historical information into account.

FIG. 5 is an illustration of an example of a weighting policy 500 shared by a community of users according to an embodiment. The example illustrates that a potential route may be given a lower priority if it has been previously followed by the user. Moreover, the system may assign higher weight to feedback provided by the athlete using the system (User 1). For example, as illustrated in the policy 500, when the potential route is previously followed by the User 1, the system may assign a lowest weight (e.g., "0"). In another example, when the potential route was not previously followed by User 1, the system may assign a lowest highest weight (e.g., "1"). In another example, when the potential route was not previously followed by User 1 and the source of the potential route is an athlete other than User 1, the system may assign an intermediate weight (e.g., "0.8"). The weigh may therefore generally be calculated as:

Weight=$F$(Source,History).

Figure 6A:
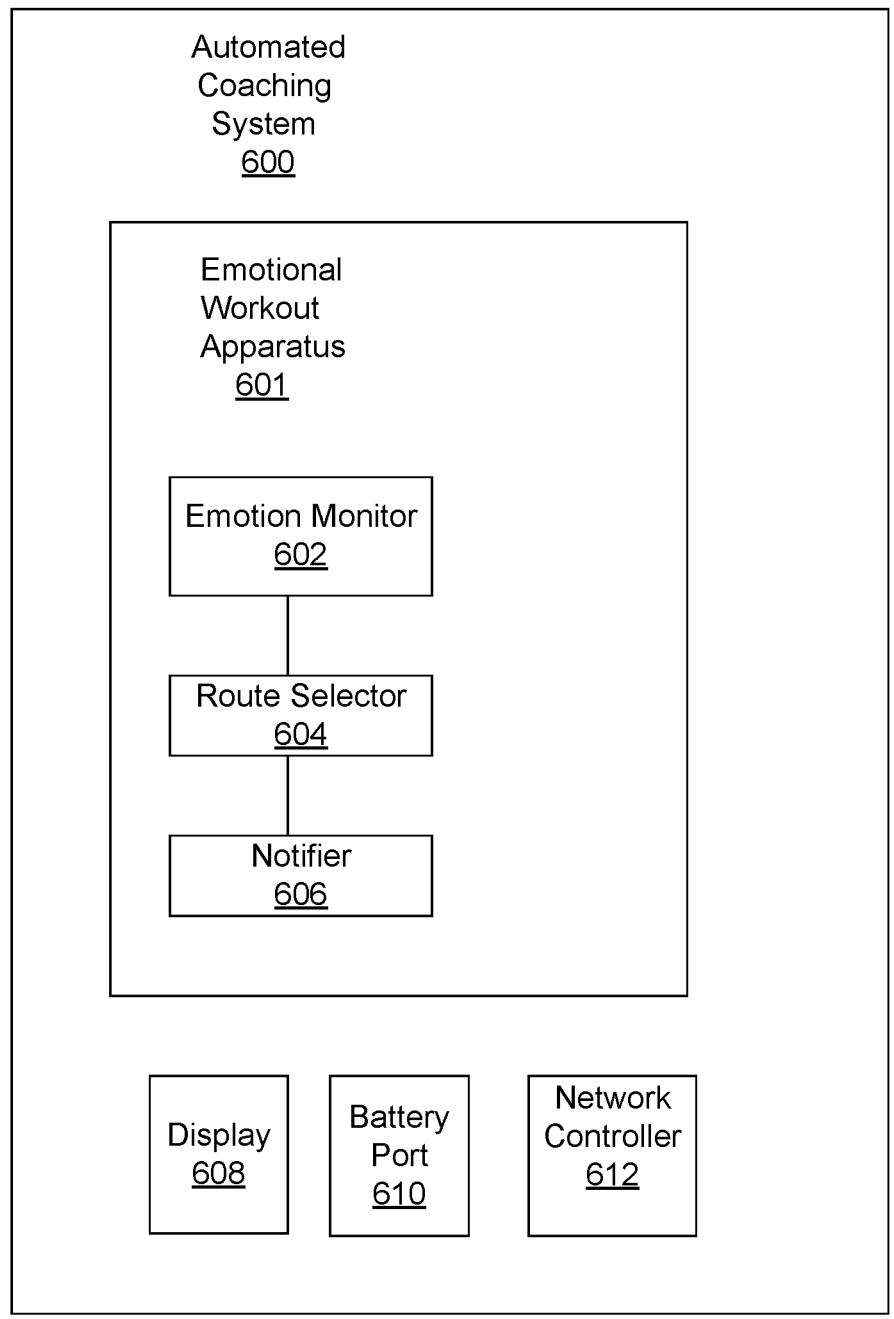
FIG. 6A is a block diagram of an example of an automated coaching system according to an embodiment.

FIG. 6A shows an automated coaching system 600 for an emotional workout according to an embodiment. The system 600 may generally implement one or more aspects of the method 201 (FIG. 2) and/or the method 300 (FIG. 3), already discussed. In the illustrated example, an emotional workout apparatus 601 includes an emotion monitor 602 that determines an emotional state of a user. The apparatus 601 may also include a route selector 604 communicatively coupled to the emotion monitor 602, wherein the route selector 604 identifies a workout route based on the emotional state of the user. Additionally, a notifier 606 communicatively coupled to the route selector 604. The notifier 606 may output the workout route via a user interface device such as, for example, a display 608, spoken dialogue system (not shown), and so forth. The system 600 may also include a battery port 610 to obtain power for the device and a network controller 612 to facilitate communications between the system 600 and other devices (not shown). The emotional workout apparatus 601 may include logic instructions, configurable logic, fixed-functionality logic hardware, etc., or any combination thereof.

Figure 6B:
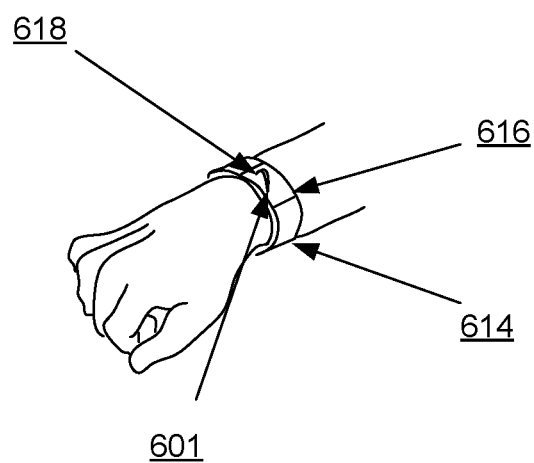
FIG. 6B is an illustration of an automated coaching system including a housing with a wearable form factor according to an embodiment.

FIG. 6B shows an automated coaching system 600 including a housing 614 with a wearable form factor. The wearable form factor may be, for example, a wrist watch, jewelry, eyewear, headwear, clothing, footwear or other wearable form factor, depending on the circumstances. In an embodiment, the wearable form factor system, for example, has a weight of under 6 ounces. The coaching system 600 may also include a user interface device 616 that includes a display 618. The display 618 may visually present a workout route suggested by the coaching system, wherein the coaching system 600 may also include the emotional workout apparatus 601, already discussed.

Figure 7:
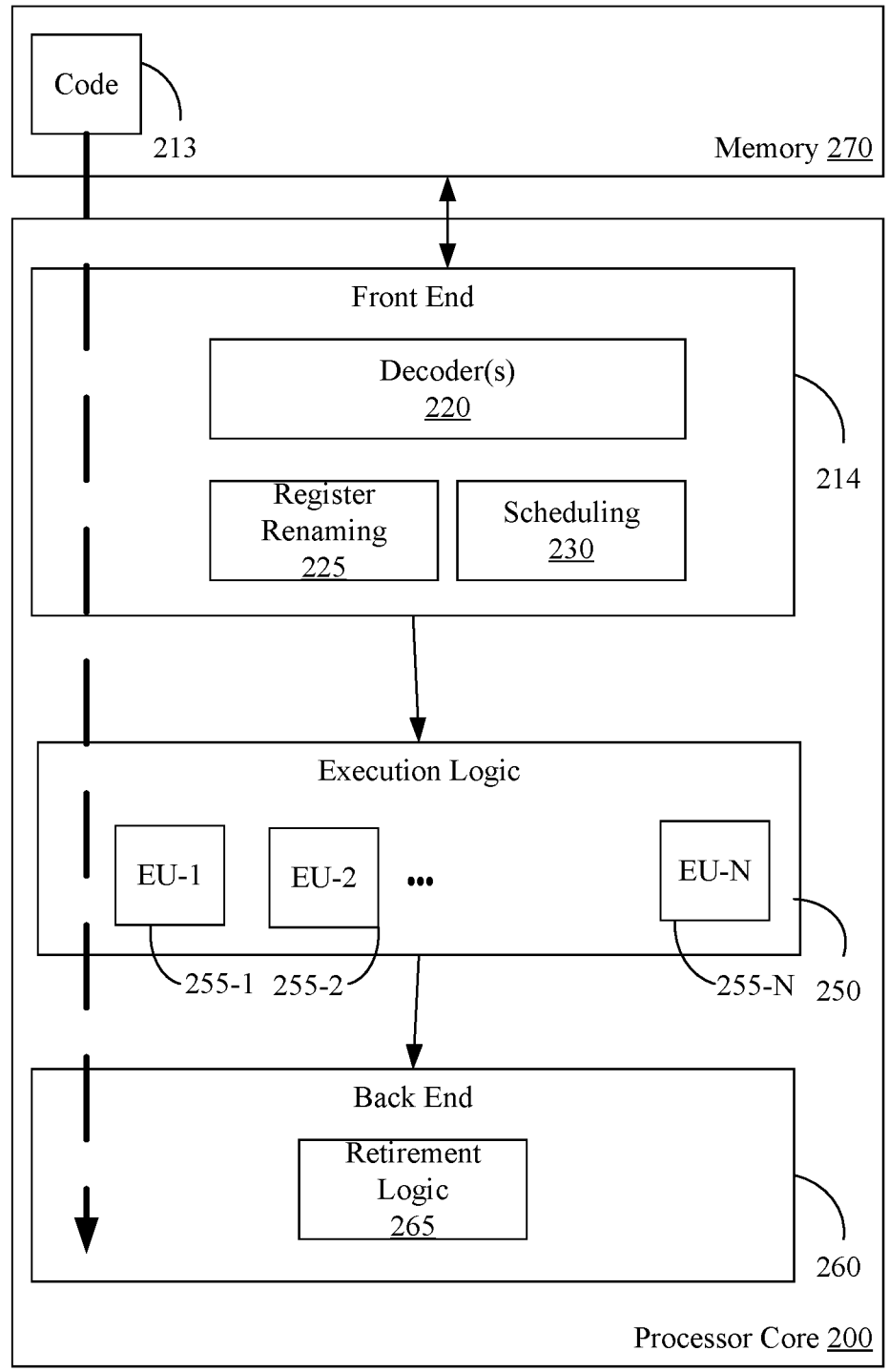
FIG. 7 is a block diagram of an example of a processor according to an embodiment.

FIG. 7 illustrates a processor core 200 according to one embodiment. The processor core 200 may be the core for any type of processor, such as a micro-processor, an embedded processor, a digital signal processor (DSP), a network processor, or other device to execute code. Although only one processor core 200 is illustrated in FIG. 7, a processing element may alternatively include more than one of the processor core 200 illustrated in FIG. 7. The processor core 200 may be a single-threaded core or, for at least one embodiment, the processor core 200 may be multithreaded in that it may include more than one hardware thread context (or "logical processor") per core.

FIG. 7 also illustrates a memory 270 coupled to the processor core 200. The memory 270 may be any of a wide variety of memories (including various layers of memory hierarchy) as are known or otherwise available to those of skill in the art. The memory 270 may include one or more code 213 instruction(s) to be executed by the processor core 200, wherein the code 213 may implement the method 201 (FIG. 2) and/or the method 300 (FIG. 3), already discussed. The processor core 200 follows a program sequence of instructions indicated by the code 213. Each instruction may enter a front end portion 214 and be processed by one or more decoders 220. The decoder 220 may generate as its output a micro operation such as a fixed width micro operation in a predefined format, or may generate other instructions, microinstructions, or control signals which reflect the original code instruction. The illustrated front end portion 214 also includes register renaming logic 225 and scheduling logic 230, which generally allocate resources and queue the operation corresponding to the convert instruction for execution.

The processor core 200 is shown including execution logic 250 having a set of execution units 255-1 through 255-N. Some embodiments may include a number of execution units dedicated to specific functions or sets of functions. Other embodiments may include only one execution unit or one execution unit that can perform a particular function. The illustrated execution logic 250 performs the operations specified by code instructions.

After completion of execution of the operations specified by the code instructions, back end logic 260 retires the instructions of the code 213. In one embodiment, the processor core 200 allows out of order execution but requires in order retirement of instructions. Retirement logic 265 may take a variety of forms as known to those of skill in the art (e.g., re-order buffers or the like). In this manner, the processor core 200 is transformed during execution of the code 213, at least in terms of the output generated by the decoder, the hardware registers and tables utilized by the register renaming logic 225, and any registers (not shown) modified by the execution logic 250.

Although not illustrated in FIG. 7, a processing element may include other elements on chip with the processor core 200. For example, a processing element may include memory control logic along with the processor core 200. The processing element may include I/O control logic and/or may include I/O control logic integrated with memory control logic. The processing element may also include one or more caches.

Figure 8:
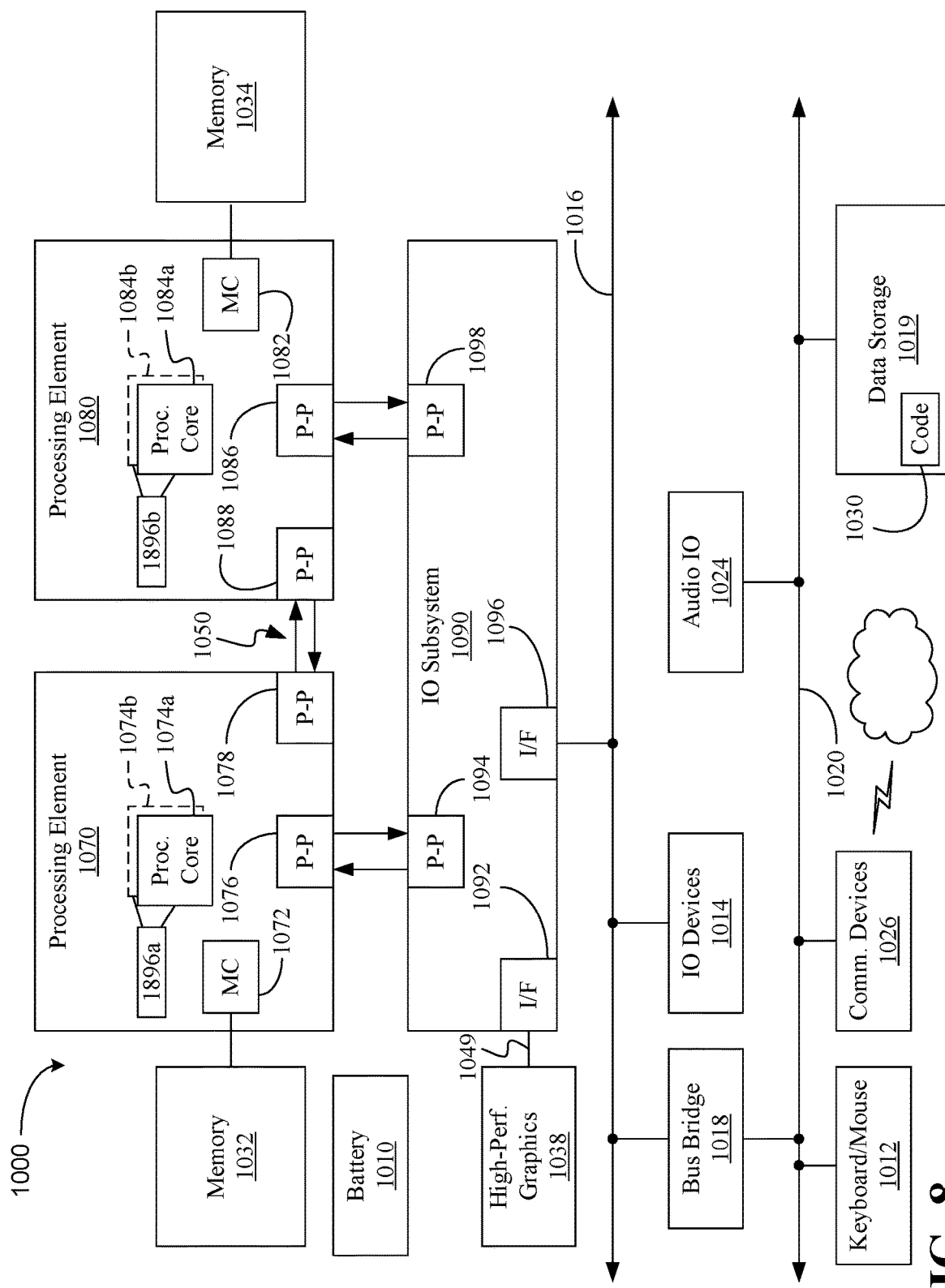
FIG. 8 is a block diagram of an example of a system according to an embodiment.

Referring now to FIG. 8, shown is a block diagram of a system 1000 embodiment in accordance with an embodiment. Shown in FIG. 8 is a multiprocessor system 1000 that includes a first processing element 1070 and a second processing element 1080. While two processing elements 1070 and 1080 are shown, it is to be understood that an embodiment of the system 1000 may also include only one such processing element.

The system 1000 is illustrated as a point-to-point interconnect system, wherein the first processing element 1070 and the second processing element 1080 are coupled via a point-to-point interconnect 1050. It should be understood that any or all of the interconnects illustrated in FIG. 8 may be implemented as a multi-drop bus rather than point-to-point interconnect.

As shown in FIG. 8, each of processing elements 1070 and 1080 may be multicore processors, including first and second processor cores (i.e., processor cores 1074*a* and 1074*b* and processor cores 1084*a* and 1084*b*). Such cores 1074*a*, 1074*b*, 1084*a*, 1084*b* may be configured to execute instruction code in a manner similar to that discussed above in connection with FIG. 7.

Each processing element 1070, 1080 may include at least one shared cache 1896*a*, 1896*b* (e.g., static random access memory/SRAM). The shared cache 1896*a*, 1896*b* may store data (e.g., objects, instructions) that are utilized by one or more components of the processor, such as the cores 1074*a*, 1074*b* and 1084*a*, 1084*b*, respectively. For example, the shared cache 1896a, 1896b may locally cache data stored in a memory 1032, 1034 for faster access by components of the processor. In one or more embodiments, the shared cache 1896a, 1896b may include one or more mid-level caches, such as level 2 (L2), level 3 (L3), level 4 (L4), or other levels of cache, a last level cache (LLC), and/or combinations thereof.

While shown with only two processing elements 1070, 1080, it is to be understood that the scope of the embodiments are not so limited. In other embodiments, one or more additional processing elements may be present in a given processor. Alternatively, one or more of processing elements 1070, 1080 may be an element other than a processor, such as an accelerator or a field programmable gate array. For example, additional processing element(s) may include additional processors(s) that are the same as a first processor 1070, additional processor(s) that are heterogeneous or asymmetric to processor a first processor 1070, accelerators (such as, e.g., graphics accelerators or digital signal processing (DSP) units), field programmable gate arrays, or any other processing element. There can be a variety of differences between the processing elements 1070, 1080 in terms of a spectrum of metrics of merit including architectural, micro architectural, thermal, power consumption characteristics, and the like. These differences may effectively manifest themselves as asymmetry and heterogeneity amongst the processing elements 1070, 1080. For at least one embodiment, the various processing elements 1070, 1080 may reside in the same die package.

The first processing element 1070 may further include memory controller logic (MC) 1072 and point-to-point (P-P) interfaces 1076 and 1078. Similarly, the second processing element 1080 may include a MC 1082 and P-P interfaces 1086 and 1088. As shown in FIG. 8, MC's 1072 and 1082 couple the processors to respective memories, namely a memory 1032 and a memory 1034, which may be portions of main memory locally attached to the respective processors. While the MC 1072 and 1082 is illustrated as integrated into the processing elements 1070, 1080, for alternative embodiments the MC logic may be discrete logic outside the processing elements 1070, 1080 rather than integrated therein.

The first processing element 1070 and the second processing element 1080 may be coupled to an I/O subsystem 1090 via P-P interconnects 1076 1086, respectively. As shown in FIG. 4, the I/O subsystem 1090 includes P-P interfaces 1094 and 1098. Furthermore, I/O subsystem 1090 includes an interface 1092 to couple I/O subsystem 1090 with a high-performance graphics engine 1038. In one embodiment, bus 1049 may be used to couple the graphics engine 1038 to the I/O subsystem 1090. Alternately, a point-to-point interconnect may couple these components.

In turn, I/O subsystem 1090 may be coupled to a first bus 1016 via an interface 1096. In one embodiment, the first bus 1016 may be a Peripheral Component Interconnect (PCI) bus, or a bus such as a PCI Express bus or another third generation I/O interconnect bus, although the scope of the embodiments are not so limited.

As shown in FIG. 8, various I/O devices 1014 (e.g., cameras, sensors) may be coupled to the first bus 1016, along with a bus bridge 1018 which may couple the first bus 1016 to a second bus 1020. In one embodiment, the second bus 1020 may be a low pin count (LPC) bus. Various devices may be coupled to the second bus 1020 including, for example, a keyboard/mouse 1012, network controllers/communication device(s) 1026 (which may in turn be in communication with a computer network), and a data storage unit 1019 such as a disk drive or other mass storage device which may include code 1030, in one embodiment. The code 1030 may include instructions for performing embodiments of one or more of the methods described above. Thus, the illustrated code 1030 may implement the method 201 (FIG. 2) and/or the method 300 (FIG. 3), already discussed, and may be similar to the code 213 (FIG. 7), already discussed. The system 1000 may also include an emotional workout apparatus such as, for example, the apparatus 601 (FIG. 6). Further, an audio I/O 1024 may be coupled to second bus 1020.

Note that other embodiments are contemplated. For example, instead of the point-to-point architecture of FIG. 8, a system may implement a multi-drop bus or another such communication topology. Also, the elements of FIG. 8 may alternatively be partitioned using more or fewer integrated chips than shown in FIG. 8. Moreover, the network controllers/communication device(s) 1026 may be implemented as a HFI (host fabric interface), also known as NIC (network interface card), that is integrated with one or more of the processing elements 1070, 1080 either on the same die, or in the same package.

ADDITIONAL NOTES AND EXAMPLES

Example 1 may include a system to improve workout experiences, comprising a housing having a wearable form factor, a user interface device, and an emotion monitor to determine an emotional state of a user, a route selector communicatively coupled to the emotion monitor, the route selector to identify a workout route based on the emotional state of the user; and a notifier communicatively coupled to the route selector, the notifier to output the workout route via the user interface device.

Example 2 may include the system of Example 1, wherein the emotional monitor to determine the emotional state of the user further includes inferring emotions from one or more of sensor information or user speech information, wherein the sensor information includes one or more of blood pressure signals, heart rate signals or sweat measurement signals, and wherein the user speech information includes one or more of words used in an input utterance or a prosody of the input utterance.

Example 3 may include the system of Example 1, wherein the route selector further including updating the workout route during a workout session that implements the workout route based on a change in the emotional state of the user.

Example 4 may include the system of any one of Examples 1 to 3, wherein the route selector further including searching a list of previously stored routes for one or more tags associated with the emotional state of the user.

Example 5 may include an emotional workout apparatus comprising, comprising an emotion monitor to determine an emotional state of a user, a route selector communicatively coupled to the emotion monitor, the route selector to identify a workout route based on the emotional state of the user, and a notifier communicatively coupled to the route selector, the notifier to output the workout route via a user interface device.

Example 6 may include the apparatus of Example 5, wherein the emotional monitor to determine the emotional state of the user further includes to infer emotions from one or more of sensor information or user speech information, wherein the sensor information is to include one or more of blood pressure signals, heart rate signals or sweat measurement signals, and wherein the user speech information is to include one or more of words used in an input utterance or a prosody of the input utterance.

Example 7 may include the apparatus of Example 5, wherein the route selector further including updating the workout route during a workout session that implements the workout route based on a change in the emotional state of the user.

Example 8 may include the apparatus of Example 5, wherein the route selector further includes searching a list of previously stored routes for one or more tags associated with the emotional state of the user.

Example 9 may include the apparatus of Example 8, wherein the road selector further identifies one or more routes in the list that have been previously followed by the user, and prevents the one or more routes from being identified as the workout route.

Example 10 may include the apparatus of Example 8, wherein the road selector further creates the list of previously stored routes based on preconfigured routes and associated tags shared by a plurality of users.

Example 11 may include the apparatus of Example 8, wherein the road selector gives a higher weight to tags shared by the user than tags shared by other users.

Example 12 may include apparatus of any one of Examples 5-11, wherein tags in the list of previously stored routes by the road selector describe factors relevant to an emotional perception of the route.

Example 13 may include a method of operating an emotional workout apparatus, comprising determining an emotional state of a user, identifying a workout route based on the emotional state of the user, and outputting the workout route via a user interface device.

Example 14 may include the method of Example 13, wherein determining the emotional state of the user includes inferring emotions from one or more of sensor information or user speech information, wherein the sensor information includes one or more of blood pressure signals, heart rate signals or sweat measurement signals, and wherein the user speech information includes one or more of words used in an input utterance or a prosody of the input utterance.

Example 15 may include the method of Example 13, further including updating the workout route during a workout session that implements the workout route based on a change in the emotional state of the user.

Example 16 of any one of Example 13-15, further including searching a list of previously stored routes for one or more tags associated with the emotional state of the user.

Example 17 may include at least one non-transitory computer readable storage medium comprising a set of instructions which, if executed by a computing device, cause the computing device to determine an emotional state of a user, identify a workout route based on the emotional state of the user, and output the workout route via a user interface device.

Example 18 may include the at least one non-transitory computer readable storage medium of Example 17, wherein the instructions, if executed, cause a computing device to infer emotions from one or more of sensor information or user speech information, wherein the sensor information is to include one or more of blood pressure signals, heart rate signals or sweat measurement signals, and wherein the user speech information is to include one or more of words used in an input utterance or a prosody of the input utterance.

Example 19 may include the at least one non-transitory computer readable storage medium of Example 17, wherein the instructions, if executed, cause a computing device to update the workout route during a workout session that implements the workout route based on a change in the emotional state of the user.

Example 20 may include the at least one non-transitory computer readable storage medium of Example 17, wherein the instructions, if executed, cause a computing device to search a list of previously stored routes for one or more tags associated with the emotional state of the user.

Example 21 may include the at least one non-transitory computer readable storage medium of Example 20, wherein the instructions, if executed, cause a computing device to identify one or more routes in the list that have been previously followed by the user, and prevent the one or more routes from being identified as the workout route.

Example 22 may include the at least one non-transitory computer readable storage medium of Example 20, wherein the instructions, if executed, cause a computing device to create the list of previously stored routes based on preconfigured routes and associated tags shared by a plurality of users.

Example 23 may include the at least one non-transitory computer readable storage medium of Example 20, wherein the instructions, if executed, cause a computing device to give a higher weight to tags shared by the user than tags shared by other users.

Example 24 may include the at least one non-transitory computer readable storage medium of any of Examples 17-23, wherein tags in the list of previously stored routes describe factors relevant to an emotional perception of the route.

Example 25 may include an emotional workout apparatus, comprising means for determining an emotional state of a user, means for identifying a workout route based on the emotional state of the user, and means for outputting the workout route via a user interface device.

Example 26 may include the apparatus of Example 25, wherein means for determining the emotional state of the user includes inferring emotions from one or more of sensor information or user speech information, wherein the sensor information includes one or more of blood pressure signals, heart rate signals or sweat measurement signals, and wherein the user speech information includes one or more of words used in an input utterance or a prosody of the input utterance.

Example 27 may include the apparatus of Example 25, further including means for updating the workout route during a workout session that implements the workout route based on a change in the emotional state of the user.

Example 28 may include the apparatus of any one of Example 25-27, further including means for searching a list of previously stored routes for one or more tags associated with the emotional state of the user.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" may mean any combination of the listed terms. For example, the phrases "one or more of A, B or C" may mean A; B; C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. A system comprising:
   a housing having a wearable form factor;
   a user interface device; and
   an emotional workout apparatus including:
      an emotion monitor to determine an emotional state of a user;
      a route selector communicatively coupled to the emotion monitor, the route selector to identify a workout route based on the emotional state of the user, wherein the workout route is to be selected from an emotional map of pre-classified potential routes including a relaxing route, a regular workout route and a route that was not previously taken; and
      a notifier communicatively coupled to the route selector, the notifier to output the workout route via the user interface device.

2. The system of claim 1, wherein the emotional monitor to determine the emotional state of the user further includes inferring emotions from one or more of sensor information or user speech information, wherein the sensor information includes one or more of blood pressure signals, heart rate signals or sweat measurement signals to be processed by a sentiment analyzer to indicate the emotional state of the user via an output of the sentiment analyzer, and wherein the user speech information includes one or more of words used in an input utterance or a prosody of the input utterance to be processed by the sentiment analyzer to indicate the emotional state of the user via an output of the sentiment analyzer.

3. The system of claim 1, wherein the route selector further including updating the workout route during a workout session that implements the workout route based on a change in the emotional state of the user.

4. The system of claim 1, wherein the route selector further including searching a list of previously stored routes for one or more tags associated with the emotional state of the user, wherein a tag of the one or more tags indicates a feature of an associated route that is relevant to address the emotional state of the user.

5. An apparatus comprising:
   an emotion monitor to determine an emotional state of a user;
   a route selector communicatively coupled to the emotion monitor, the route selector to identify a workout route based on the emotional state of the user, wherein the workout route is to be selected from an emotional map of pre-classified potential routes including a relaxing route, a regular workout route and a route that was not previously taken; and
   a notifier communicatively coupled to the route selector, the notifier to output the workout route via a user interface device.

6. The apparatus of claim 5, wherein the emotional monitor to determine the emotional state of the user further includes to infer emotions from one or more of sensor information or user speech information, wherein the sensor information is to include one or more of blood pressure signals, heart rate signals or sweat measurement signals to be processed by a sentiment analyzer to indicate the emotional state of the user via an output of the sentiment analyzer, and wherein the user speech information is to include one or more of words used in an input utterance or a prosody of the input utterance to be processed by the sentiment analyzer to indicate the emotional state of the user via an output of the sentiment analyzer.

7. The apparatus of claim 5, wherein the route selector further including updating the workout route during a workout session that implements the workout route based on a change in the emotional state of the user.

8. The apparatus of claim 5, wherein the route selector further includes searching a list of previously stored routes for one or more tags associated with the emotional state of the user, wherein a tag of the one or more tags indicates a feature of an associated route that is relevant to address the emotional state of the user.

9. The apparatus of claim 8, wherein the road selector further creates the list of previously stored routes based on preconfigured routes and associated tags shared by a plurality of users.

10. The apparatus of claim 8, wherein the road selector gives a higher weight to tags shared by the user than tags shared by other users.

11. The apparatus of claim 8, wherein tags in the list of previously stored routes by the road selector are keywords relevant to an emotional perception of the route.

12. A method comprising:
    determining, via an emotion monitor, an emotional state of a user;
    identifying, via a route selector in communication with the emotion monitor, a workout route based on the emotional state of the user, wherein the workout route is to be selected from an emotional map of pre-classified potential routes including a relaxing route, a regular workout route and a route that was not previously taken; and
    outputting the workout route via a user interface device.

13. The method of claim 12, wherein determining the emotional state of the user includes inferring emotions from one or more of sensor information or user speech information, wherein the sensor information includes one or more of blood pressure signals, heart rate signals or sweat measurement signals processed by a sentiment analyzer to indicate the emotional state of the user via an output of the sentiment analyzer, and wherein the user speech information includes one or more of words used in an input utterance or a prosody of the input utterance processed by the sentiment analyzer to indicate the emotional state of the user via an output of the sentiment analyzer.

14. The method of claim 12, further including updating the workout route during a workout session that implements the workout route based on a change in the emotional state of the user.

15. The method of claim 12, further including searching the list of previously stored routes for one or more tags associated with the emotional state of the user, wherein a tag of the one or more tags indicates a feature of an associated route that is relevant to address the emotional state of the user.

16. At least one non-transitory computer readable storage medium comprising a set of instructions which, if executed by a computing device, cause the computing device to:
    determine an emotional state of a user;
    identify a workout route based on the emotional state of the user, wherein the workout route is to be selected from an emotional map of pre-classified potential routes including a relaxing route, a regular workout route and a route that was not previously taken; and
    output the workout route via a user interface device.

17. The at least one non-transitory computer readable storage medium of claim 16, wherein the instructions, if executed, cause a computing device to infer emotions from one or more of sensor information or user speech information to be processed by a sentiment analyzer to indicate the emotional state of the user via an output of the sentiment analyzer, wherein the sensor information is to include one or more of blood pressure signals, heart rate signals or sweat measurement signals, and wherein the user speech information is to include one or more of words used in an input utterance or a prosody of the input utterance to be processed by the sentiment analyzer to indicate the emotional state of the user via an output of the sentiment analyzer.

18. The at least one non-transitory computer readable storage medium of claim 16, wherein the instructions, if executed, cause a computing device to update the workout route during a workout session that implements the workout route based on a change in the emotional state of the user.

19. The at least one non-transitory computer readable storage medium of claim 16, wherein the instructions, if executed, cause a computing device to search the list of previously stored routes for one or more tags associated with the emotional state of the user, wherein a tag of the one or more tags indicates a feature of an associated route that is relevant to address the emotional state of the user.

20. The at least one non-transitory computer readable storage medium of claim 19, wherein the instructions, if executed, cause a computing device to create the list of previously stored routes based on preconfigured routes and associated tags shared by a plurality of users.

21. The at least one non-transitory computer readable storage medium of claim 19, wherein the instructions, if executed, cause a computing device to give a higher weight to tags shared by the user than tags shared by other users.

22. The at least one non-transitory computer readable storage medium of claim 19, wherein tags in the list of previously stored routes are keywords relevant to an emotional perception of the route.

23. The apparatus of claim 5, wherein a weight used to determine whether to select the route is based on an identification of a source of user feedback corresponding to a candidate route and an identification of whether the candidate route is previously followed.

24. The apparatus of claim 23, wherein a first weight is determined when there is an identification of the user as the source of user feedback and an identification of the candidate route as not previously followed by the user, wherein a second weight opposite to the first weight is determined when there is an identification of any user as the source of the user feedback and an identification of the candidate route as previously followed by the user, and wherein a third weight between the first weight and the second weight is determined where there is an identification of another user as the source of user feedback and an identification of the candidate route as not previously followed by the user.

25. The apparatus of claim 8, wherein the road selector further identifies one or more routes in the list that have been previously followed by the user, and prevents the one or more routes from being identified as the workout route.

26. The at least one non-transitory computer readable storage medium of claim 19, wherein the instructions, if executed, cause a computing device to:
    identify one or more routes in the list that have been previously followed by the user; and
    prevent the one or more routes from being identified as the workout route.

* * * * *